(12) United States Patent
Kozersky

(10) Patent No.: US 8,758,284 B1
(45) Date of Patent: Jun. 24, 2014

(54) CONVERTIBLE ORTHOTIC BRACE

(75) Inventor: David J. Kozersky, Columbus, OH (US)

(73) Assignee: Capital Prosthetic and Orthotic Center, Inc., Columbus, OH (US)

( * ) Notice: Subject to any disclaimer, the term of this patent is extended or adjusted under 35 U.S.C. 154(b) by 45 days.

(21) Appl. No.: 13/492,363

(22) Filed: Jun. 8, 2012

Related U.S. Application Data

(60) Provisional application No. 61/494,550, filed on Jun. 8, 2011.

(51) Int. Cl.
*A61F 5/00* (2006.01)
(52) U.S. Cl.
USPC ................................. 602/19; 602/5
(58) Field of Classification Search
USPC .......... 602/5, 19; 128/95.1, 98.1, 99.1, 100.1, 128/101.1, 105.1, 106.1, 107.1; 2/311, 318
See application file for complete search history.

(56) References Cited

U.S. PATENT DOCUMENTS

| | | | | |
|---|---|---|---|---|
| 5,362,304 | A * | 11/1994 | Varn | 602/19 |
| 6,676,620 | B2 * | 1/2004 | Schwenn et al. | 602/12 |
| 6,899,689 | B1 * | 5/2005 | Modglin | 602/19 |
| 7,316,660 | B1 * | 1/2008 | Modglin | 602/5 |

\* cited by examiner

*Primary Examiner* — Michael A. Brown
(74) *Attorney, Agent, or Firm* — Roger A. Gilcrest

(57) ABSTRACT

The present invention includes an orthotic brace which offers advantages in being able to be adjusted to fit the small of the back of a specific wearer, and may be altered to be converted from a smaller LSB-type brace or a larger LSO-type brace, and may have optional ventral supports removably attachable thereto. The present invention also includes a thoraco-lumbo-sacral orthopedic (TSLO) brace variant featuring a supplementary sternal support adapted for ease of donning and removal once its strap system is fitted to the wearer.

17 Claims, 14 Drawing Sheets

CONVERTIBLE ORTHOTIC BRACE

RELATED APPLICATION DATA

This application claims the benefit of U.S. Patent Application Ser. No. 61/494,550, filed Jun. 8, 2011, which is hereby incorporated herein in its entirety by reference.

TECHNICAL FIELD FOR THE INVENTION

The present invention relates to a convertible orthotic brace and especially to a flexible orthopedic brace providing for convenient adjustment to fit a wearer by adjustment to multiple configurations.

BACKGROUND OF THE INVENTION

Several prior art orthotic braces feature front and rear panels to provide lumbar support to the patient.

For instance, in U.S. Pat. Nos. 6,478,759 and 5,967,998, hereby incorporated herein by reference, a single front support panel is attached to one or more rear panels to provide lumbar support to the patient upon closure. Devices of this type provide better support in comparison to belt-type devices. These devices may feature a reinforcement insert, typically of relatively rigid plastic, inserted into a soft material rear portion which in turn is connected to a front portion by straps.

Other braces of the prior art include those described in U.S. Pat. No. 4,202,327 having a number of straps for connecting right and left sections with the straps secured to the jacket with hook-and-loop strips. U.S. Pat. No. 4,508,110 describes a jacket-type orthoses that limits motion in the thoracic or lumbo-sacral areas and uses a rigid orthoses design that may be adjusted by a patient pulling on a plurality of laces, each attached to a short strap having hook-and-loop material thereon which is used to attach the straps to predetermined positions on the rigid brace members. Other prior art U.S. patents for orthoses include U.S. Pat. No. 4,475,543, for a lumbo-sacral brace using an elastic belt fastened with a pouch in combination with a semi-wrap-around polyurethane foam splint cured in place in the pouch; U.S. Pat. No. 2,100,964, describing a surgical belt is illustrated in which a plurality of laces are interconnected to a single strap on either side thereof; and U.S. Pat. No. 3,926,183, disclosing a dorsal lumbo sacral support combines elastic and non-elastic straps in a support device for a person's back, thoracic or pelvic areas.

U.S. Pat. No. 3,927,665 relates to a lumbo-sacral support having an elastic body encircling band and inelastic tensioning system, while U.S. Pat. No. 5,074,288 illustrates a soft body brace attached to a patient with a plurality of straps to provide a back support system with interchangeable and positionally adjustable orthotic support.

U.S. Pat. No. 4,175,553 is also a lumbo-sacral orthosis orthopedic support for encircling the torso and has a plurality of straps, and U.S. Pat. No. 4,459,979 is an orthopedic appliance made of resilient material conforming to the lower back of a person and uses a plurality of adjustable straps.

U.S. Pat. No. 5,362,304 discloses a thoracic lumbar sacral orthosis device formed as a jacket and has support plates which can attach thereto, and U.S. Pat. No. 5,188,585 concerns a lumbo-sacral orthopedic support which encircles the torso of a patient and has adjustable strap portions. U.S. Pat. No. 4,559,933 describes an orthopedic lumbo-sacral corset using semi-rigid elements and inflatable pads.

The aforementioned patents are hereby incorporated herein by reference.

One of the problems with orthotic braces of the prior art is that they cannot be used as both a smaller lumbosacral belt ("LSB") type orthotic brace and as a relatively larger lumbosacral orthotic ("LSO") type brace.

Accordingly, it is desirable to provide an orthotic device that allows for the relatively convenient conversion between a smaller LSB type orthotic brace and as a relatively larger LSO type brace.

In addition, it is also desirable to provide an LSB-LSO convertible type orthotic brace with an improved supplementary sternal support for the upper thoracic area. Such supports of the prior art are designed with a ventral support rod extending from the frontal portion of the belt. This is relatively stiff and unyielding, and can feel confining for the wearer.

Accordingly, it is desirable to provide effective supplementary sternal support without relying upon a support that extends from the wearers front while providing equivalent supplementary sternal support.

In addition, it is normally inconvenient for wearers to be able to don and remove such a supplementary sternal support without disrupting the custom fitting of its attachment to the wearer. Thus, in this regard, it is also beneficial to provide such a supplementary sternal support that may be readily donned and removed by the wearer without the need to reposition the fitments that position the supplementary sternal support.

Accordingly, in light of the aforementioned shortcomings of currently available orthotic braces, there is a need for a convertible lumbar orthosis which can be adjusted on the patient so as to provide optional LSB- or LSO-type support while conforming to the back of a patient to provide a more customized fit.

In addition, there remains a need for LSO-type devices that permit the optional use of a supplementary sternal support without sacrificing comfort and ease of donning and removal while maintaining its customized fitting and support settings, such as by having to rearrange the straps of the brace.

SUMMARY OF THE INVENTION

The present invention includes an orthotic brace which offers advantages in being able to be adjusted to fit the small of the back of a specific wearer, and may be altered to be converted from a smaller LSB-type brace or a larger LSO-type brace, while providing effective reinforced lumbar support and comfort to the wearer.

The present invention includes a flexible lumbo-sacral orthopedic (LSO) brace which fits closely to the patient's torso while being easily attached and tightened in a wide variety of positions for a wide variety of body shapes and provides for optional ventral supports removably attachable thereto.

The present invention may also be embodied as a thoraco-lumbo-sacral orthopedic (TSLO) brace which typically has a longer rear portion and includes shoulder straps (not shown) which variation is known in the art. However, this embodiment of the present invention may optionally feature a supplementary sternal support.

Accordingly, as used herein, the term "lumbo-sacral orthopedic brace" shall be understood as including both LSO and TSLO variations.

The present invention in general terms comprises a lumbar-sacral orthosis comprising in combination, (a) a first lateral belt portion having a dorsal end having two substantially parallel horizontally extending upper and lower slots, and an inner surface bearing a pad; (b) a second lateral belt portion having a dorsal end having two substantially parallel horizontally extending upper and lower slots, and an inner surface bearing a pad; the first and second lateral belt portions adapted to overlap across the wearer's ventral area when the orthosis is donned, and to be releasably attached to one another; (c) a central dorsal portion, the central dorsal portion attached to the first and second lateral belt portions by an upper pin extending from the central dorsal portion through the upper slots, and a lower pin extending from the central dorsal portion through the lower slots, such that the longitudinal axis of each of the first and second lateral belt portions may be moved with respect to one another; the central dorsal portion comprising, along its inner-facing surface, a first rigid angled dorsal support panel, the first rigid angled support panel incorporated into the central dorsal portion such that it opens away from the wearer, when the orthosis is donned; (d) a removable secondary dorsal rigid angled support panel, larger than the first rigid angled dorsal support panel, and adapted to be nested against the first rigid angled dorsal support panel and along its inner-facing surface; (e) a removable ventral rigid support panel and adapted to be removably attached to the inside of the overlapping first and second lateral belt portions when the orthosis is donned; (f) a first strap attached to the central dorsal portion and extending over the first lateral belt portion, and adapted to be releasably attached to the ventral portion of the orthosis when donned; and (g) a second strap attached to the central dorsal portion and extending over the second lateral belt portion, and adapted to be releasably attached to the ventral portion of the orthosis when donned.

In a preferred embodiment, the removable secondary dorsal rigid angled support panel is contained in a fabric envelope and is removably nested against the first rigid angled dorsal support panel and along its inner-facing surface by hook and loop closures.

It is also preferred that the first rigid angled dorsal support panel comprises a material covering its inner surface and wherein the removable secondary dorsal rigid angled support panel is removably nested against the first rigid angled dorsal support panel and along its material-covered inner-facing surface by hook and loop closures.

As to the front of the brace, preferably the removable ventral rigid support panel is contained in a fabric envelope and is removably attached to the front of the belt and along its inner-facing surface by hook and loop closures.

It is further preferred that the orthosis additionally comprises a removable supplementary ventral support portion comprising (a) an extension portion extending anteriorly from the ventral region of the orthosis, and (b) a supplementary ventral support panel adapted to be affixed along the extension portion and to engage the wearer when the orthosis is donned.

As to the removable ventral rigid support panel, it may additionally comprise a removable supplementary ventral support portion comprising (a) an extension portion extending anteriorly from the ventral region of the orthosis, and (b) a supplementary ventral support panel adapted to be affixed along the extension portion and to engage the wearer when the orthosis is donned.

Most preferably, the supplementary ventral support panel is adapted to be fixed at two or more points along the length of the extension portion.

In a more preferred variation of this embodiment, the removable ventral rigid support panel additionally comprises a removable supplementary ventral support portion contained in a fabric envelope and attached along its inner-facing surface by hook and loop closures.

As to the first and second straps, preferably, they are adapted to be releasably attached to the ventral portion of the orthosis by hook and loop closures. In an alternative variation, the dorsal ends of the first and second lateral belt portions, and the central dorsal portion may be wrapped in a removable material envelope adapted to function as a component of a hook and loop closure. The removable material envelope may optionally be adapted to function as a component of a hook and loop closure.

The removable secondary dorsal rigid angled support panel, the first rigid angled dorsal support panel and the removable ventral rigid support panel preferably are made of or otherwise comprise a polymer material.

The orthosis of the present invention may also include a dorsal thoracic extension portion removably attached to the removable secondary dorsal rigid angled support panel; and a supplementary sternal support portion connected to the dorsal thoracic extension portion by four arm straps, two of which are adapted to extend under the wearer's arms and two of which are adapted to extend over the wearer's shoulder. In a preferred embodiment, the supplementary sternal support portion is in the form of two portions releasably connected to one another so as to allow the wearer to remove the lumbar-sacral orthosis without disconnecting the arm straps.

The present invention also includes a lumbar-sacral orthosis comprising in combination, (a) a belt portion; (b) a central dorsal portion, the central dorsal portion attached to the belt portion and comprising a central dorsal panel; (c) a dorsal thoracic extension portion removably attached to the central dorsal panel; and (d) a supplementary sternal support portion connected to the central dorsal panel by four arm straps, two of which are adapted to extend under the wearer's arms and two of which are adapted to extend over the wearer's shoulder, the supplementary sternal support portion comprising two portions releasably connected to one another so as to allow the wearer to remove the lumbar-sacral orthosis without disconnecting the arm straps.

In view of the foregoing summary and further detailed description, it will be appreciated that features of the present invention may be incorporated into an orthotic brace or belt to the extent not functionally inconsistent.

DETAILED DESCRIPTION OF THE PREFERRED EMBODIMENTS

In accordance with the foregoing summary of the invention, the following presents the preferred embodiments of the present invention, which are considered to be the best mode thereof.

Figure 1:
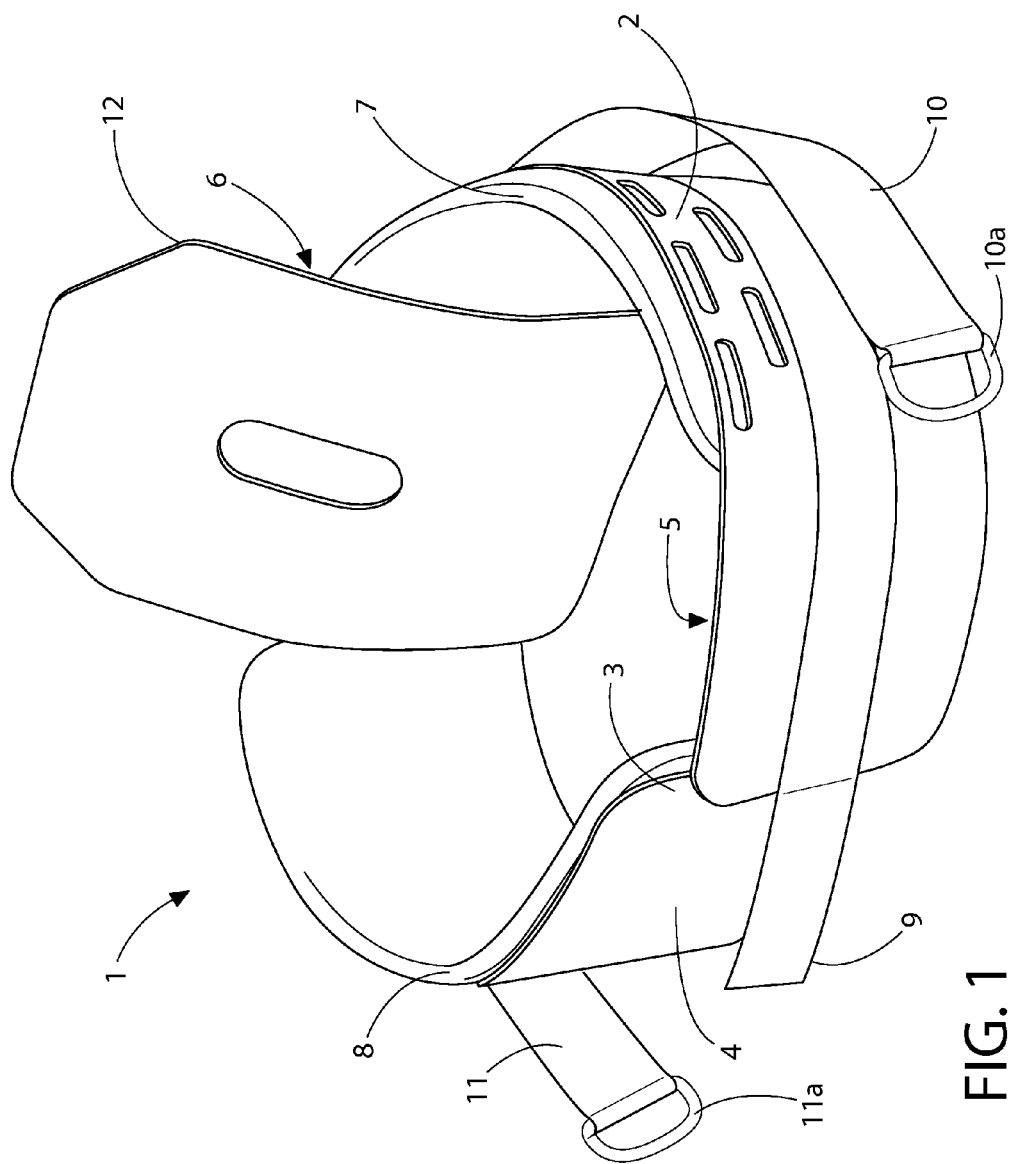
FIG. 1 is a perspective view of an orthotic brace in accordance with one embodiment of the present invention, showing the orthotic brace in an open, extended configuration, as seen from the inner side of the brace.

FIG. 1 is a plan view of an orthotic brace in accordance with one embodiment of the present invention, showing the orthotic brace in an open, extended configuration, as seen from the inner side of the brace.

FIG. 1 shows orthotic brace 1 which comprises a first lateral belt portion 2 and a second lateral belt portion 3. The first and second lateral belt portions are sized and adapted to overlap across the wearer's ventral area when the orthotic brace is donned, and to be releasably attached to one another in this region such as by virtue of opposing hook-and-loop closure portions 4 and 5 (the latter not shown in this view).

The orthotic brace 1 also comprises a central dorsal portion 6 (not shown in this view). Also shown in FIG. 1 are the optional preferred laterals pads 7 and 8.

The first and second lateral belt portions preferably are made of a flexible polymeric material such as those known and used in the art.

The support panels and portions may be made of any dimensionally stable material, typically rigid enough to provide reinforcement to the lumbar portion of the brace, such as in reinforcement inserts known and used in the art, such as through use of a polymeric material. In a preferred embodiment, and as a non-limiting example, the support panels and portions may be made of any dimensionally stable material such as ABS plastic of at least one-eighth inch in thickness.

The optional inner pad portions 7 and 8 may be constructed of any appropriate cloth or foam material (or combination thereof). This is known and used in the orthotic brace field.

In order to provide a supplementary closure, the orthotic brace 1 may also include a supplementary strap 9 which may extend from the rear portion of the brace across one of the lateral belt portions (such as lateral belt portion 2 in this embodiment), to close the front of the brace by being provided with a corresponding hook-and-loop material that is adapted to engage a hook-and-loop portion 4 in the same manner as hook-and-loop portion 5. In addition, the preferred embodiment of the orthotic brace 1 may also include tightening straps 10 and 11, which are, respectively, attached to the rear (dorsal) portions of the second lateral belt portion 3 and first lateral belt portion 2, such that when straps 10 and 11 are pulled in the forward direction by the wearer, the first and second lateral belt portions 2 and 3 are cinched tighter with respect to one another, as may be appreciated from the other Figures herein.

FIG. 1 also shows removable secondary dorsal rigid angled support panel 12 which is larger than the first rigid angled dorsal support panel incorporated into central dorsal portion 6, and is adapted to be nested against the first rigid angled dorsal support panel and along its inner-facing surface.

The first rigid angled dorsal support panel 13 may be seen in other Figures.

Figure 2:
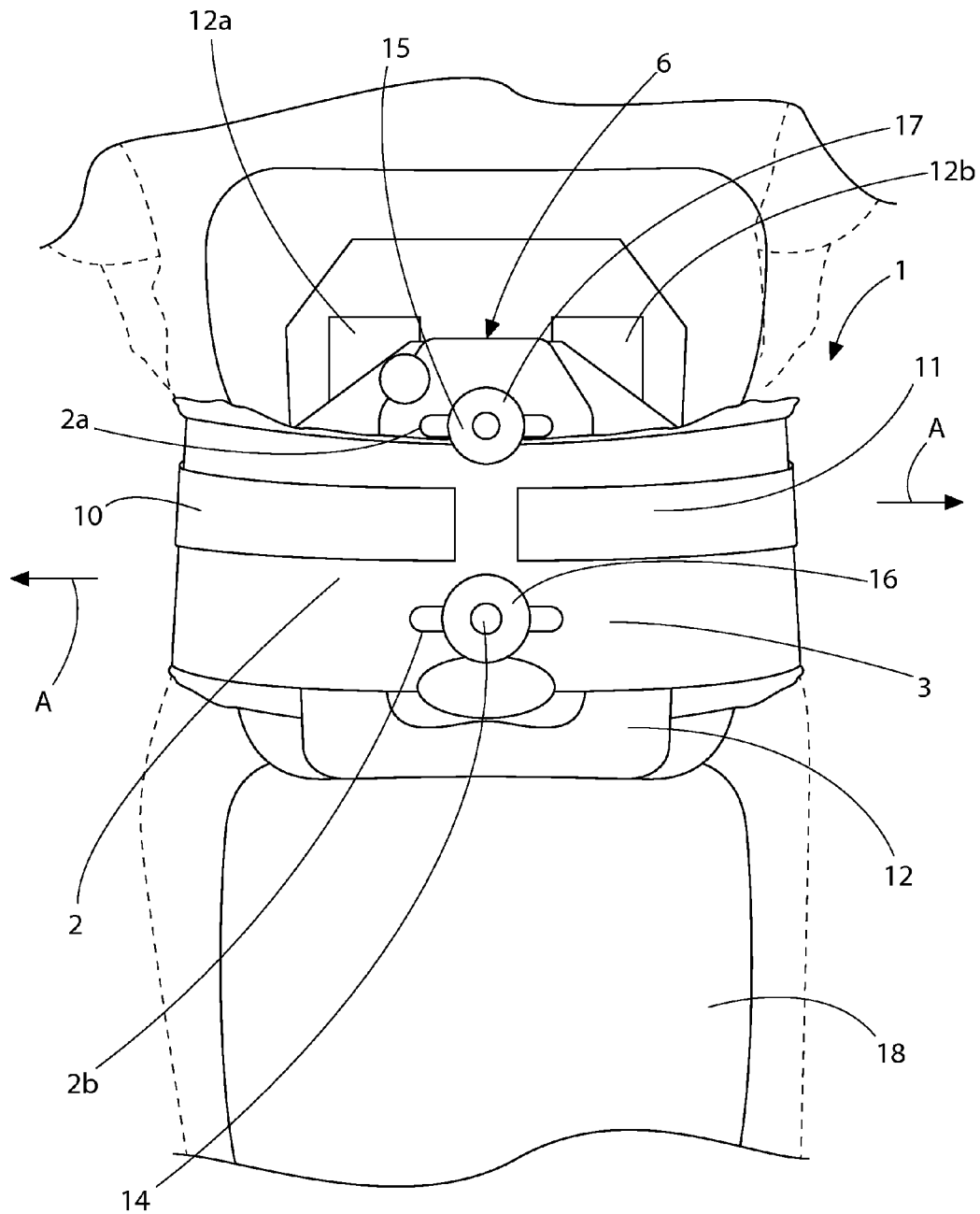
FIG. 2 is a rear elevation perspective view of an orthotic brace in accordance with one embodiment of the present invention, shown as it would be seen in a closed position on the wearer.

FIG. 2 is a rear perspective view of an orthotic brace 1 shown as it would appear when donned by a wearer, and wherein like numerals designate portions of the orthotic brace as described herein. This view shows first and second lateral belt portions 2 and 3 as well as showing the central dorsal portion 6 of the orthotic brace 1. From this Figure, one can appreciate the preferred flexible attachment arrangement in which case the first lateral belt portion 2 have two substantially parallel and horizontally extending upper and lower slots 2a and 2b located at the dorsal end thereof; and wherein the second lateral belt portion 3 is provided with two substantially parallel and horizontally extending upper and lower slots (not visible in this view), and in substantial alignment with slots 2a and 2b, in its dorsal. The arrangement and orientation of these slots allows for the placement of pins 14 and 15 through respective discs 16 and 17 (and wherein the pins 14 and 15 are also attached to similar interferent portions such as discs similar to discs 16 and 17 attached, respectively, to pins 14 and 15 and located in board of second lateral belt portion 3).

The slots 2a and 2b (as well as corresponding openings in second lateral belt portion 3), are of sufficient length and width to allow first and second lateral belt portions to be moved with respect to one another generally along the direction arrow A, as well as to allow the first and second lateral belt portions 2 and 3 to be slightly angled with respect to one another to allow the respective longitudinal axes to be angled with respect to one another. In addition, the slots preferably are sized to allow the wearer to snug the brace by pulling upon straps 10 and 11 in order to cinch the orthotic belt around the wearer's waist.

FIG. 2 also shows hook-and-loop closure panels 12a and 12b that engage corresponding hook-and-loop material on the inner surface of first rigid angled dorsal support panel 13 (designated 13a and 13b). This allows the support panels 12 and 13 to remain nested against one another.

Also shown in FIG. 2 is optional fabric envelope 18 that may be used to surround movable secondary dorsal rigid angled support panel 12.

Figure 3:
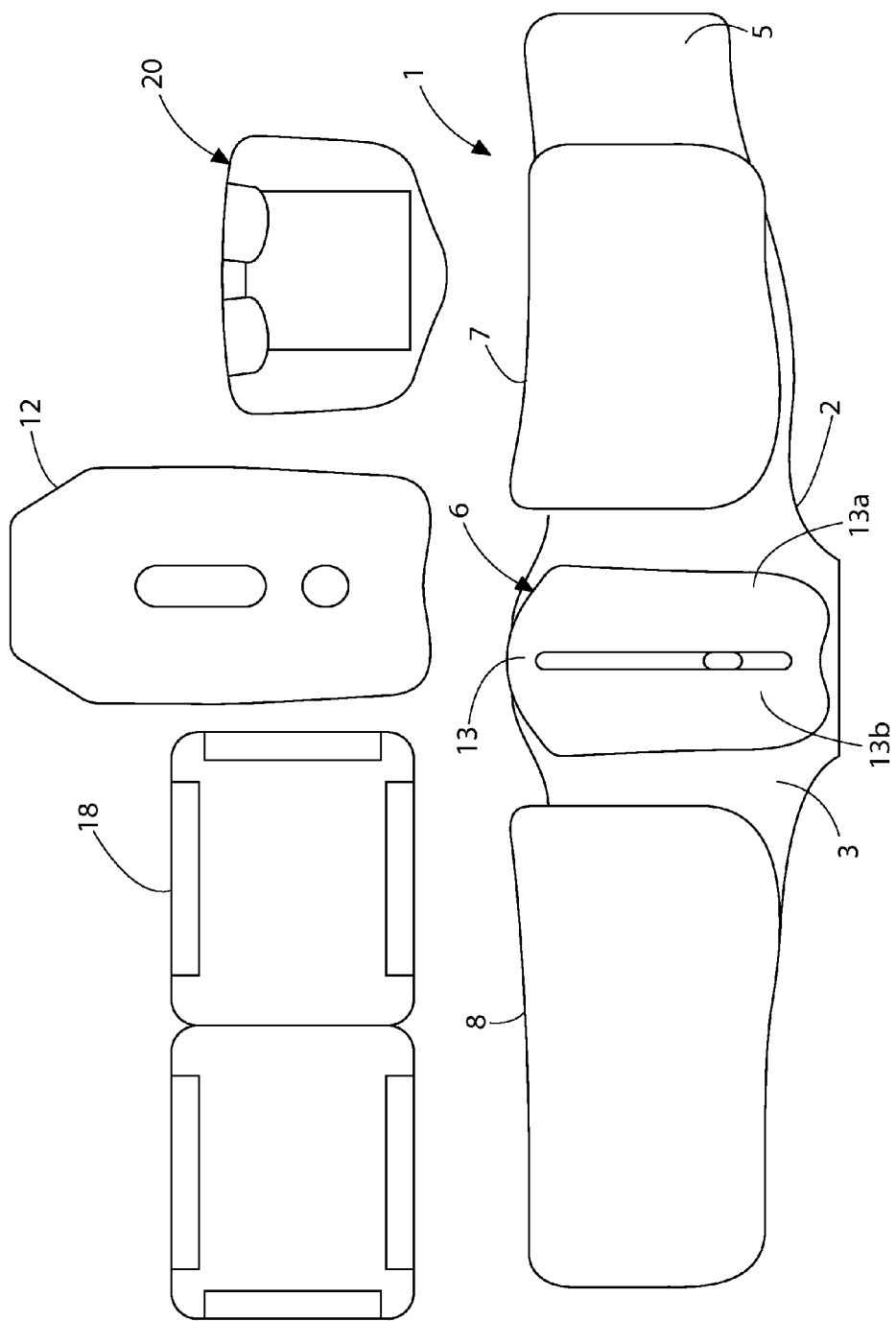
FIG. 3 is a plan view of an orthotic brace in a fully opened position, in accordance with one embodiment of the present invention.

FIG. 3 is a plan view of an orthotic brace 1 in accordance with the preferred embodiment of the invention, and wherein like referenced numerals refer to portions of the brace as already described herein. This view shows inner padding portions 7 and 8 as well as first and second lateral belt portions 2 and 3. Also visible in this view is the hook-and-loop closure portion 5 that attaches to hook-and-loop closure portion 4 as shown in FIG. 1. This view also shows the position and attachment of the first rigid angled dorsal support panel 13 as a part of the central dorsal portion 6 of the orthotic brace 1. Also seen in this view are the hook-and-loop closure panels 13a and 13b that attach, respectively, to hook-and-loop panels 12a and 12b.

This Figure shows the brace without straps 9, 10 and 11 visible.

Figure 4:
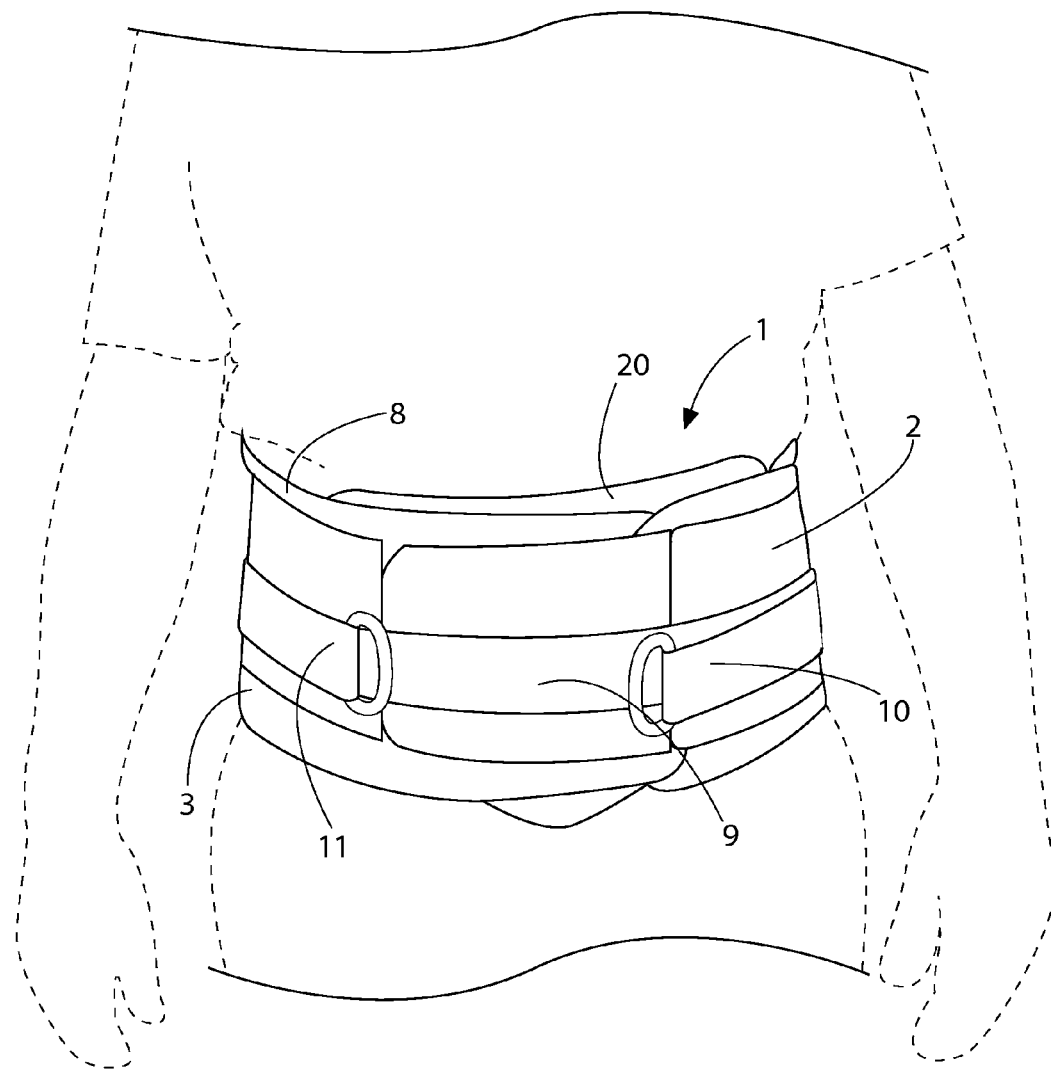
FIG. 4 is a frontal perspective view of an orthotic brace in accordance with one embodiment of the present invention, as it would be seen in a fully closed position on a wearer.

FIG. 4 is a front perspective view of an orthotic brace 1 in accordance with the preferred embodiment of the invention, as would appear once donned and closed by the wearer, and wherein like numerals refer to like portions of the brace as described herein. From this Figure, one can appreciate how the brace is closed by the overlapping of the first and second lateral belt portions 2 and 3, followed by the overlapping of supplementary belt 9 by the cinching of the first and second lateral belt portions 2 and 3 by action of straps 10 and 11 which are pulled toward the front of the belt using D-rings 10a and 11a. The inner surfaces of straps 10 and 11 are likewise provided hook-and-loop closure materials which, in the case of strap 10, attach to the outside of supplementary strap 9 and, in the case of strap 11, attach to a hook-and-loop panel such as that provided by hook-and-loop panel 4.

Figure 5:
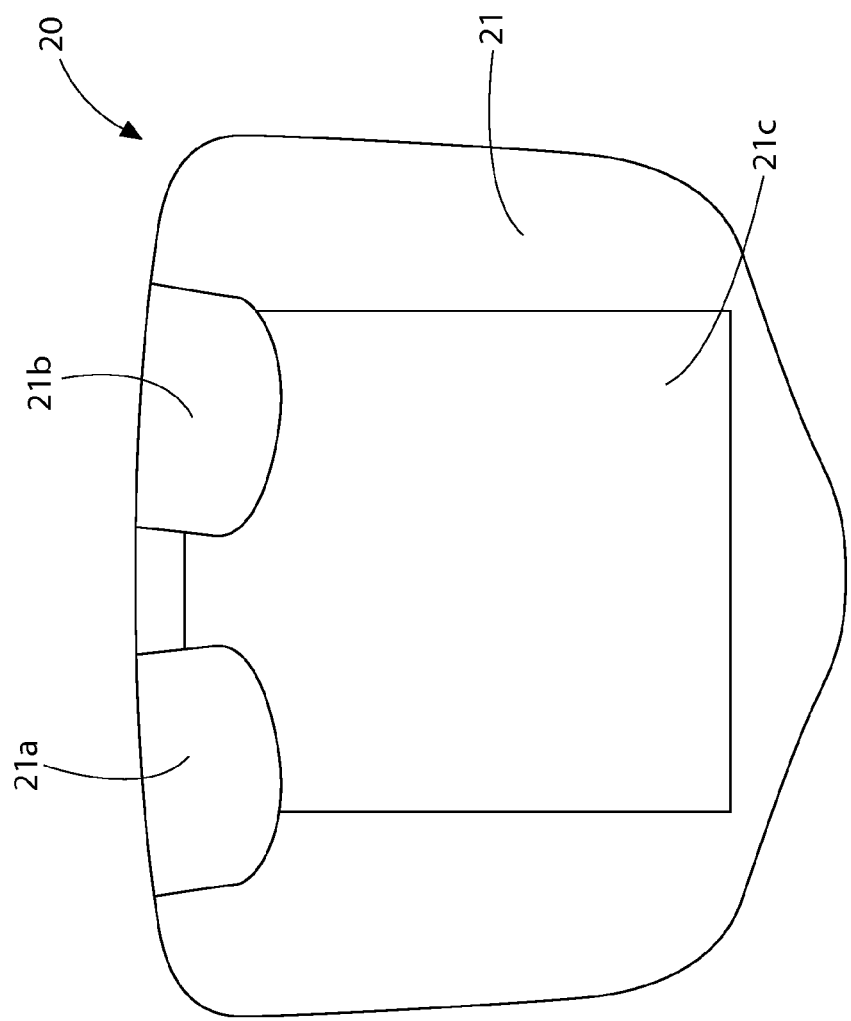
FIG. 5 is a detailed elevation view of a removable ventral rigid support panel used in accordance with a preferred embodiment of the present invention.

Also visible in FIG. 4 is a removable ventral rigid support panel 20 that is tucked inside the orthotic brace 1 prior to its closure. The removable ventral rigid support panel 20 may also preferably be enclosed in a fabric envelope similar to fabric envelope 18 for added comfort to the wearer. Removable ventral rigid support panel 20 is shown in greater detail in FIG. 5 which shows removable ventral rigid support panel 20 encased in fabric envelope 21 which, for instance, may have a slit opening along its top which may be closed by hook-and-loop flaps 21a and 21b that engage the front surface of fabric envelope 21. In addition, the front surface of fabric envelope 21 may also be provided with a hook-and-loop closure panel 21c which may attach to the inner surface of the orthotic brace, such as by being adapted to engage the inner surface(s) of fabric portions 7 and 8 of the front of the brace once closed.

Figure 6:
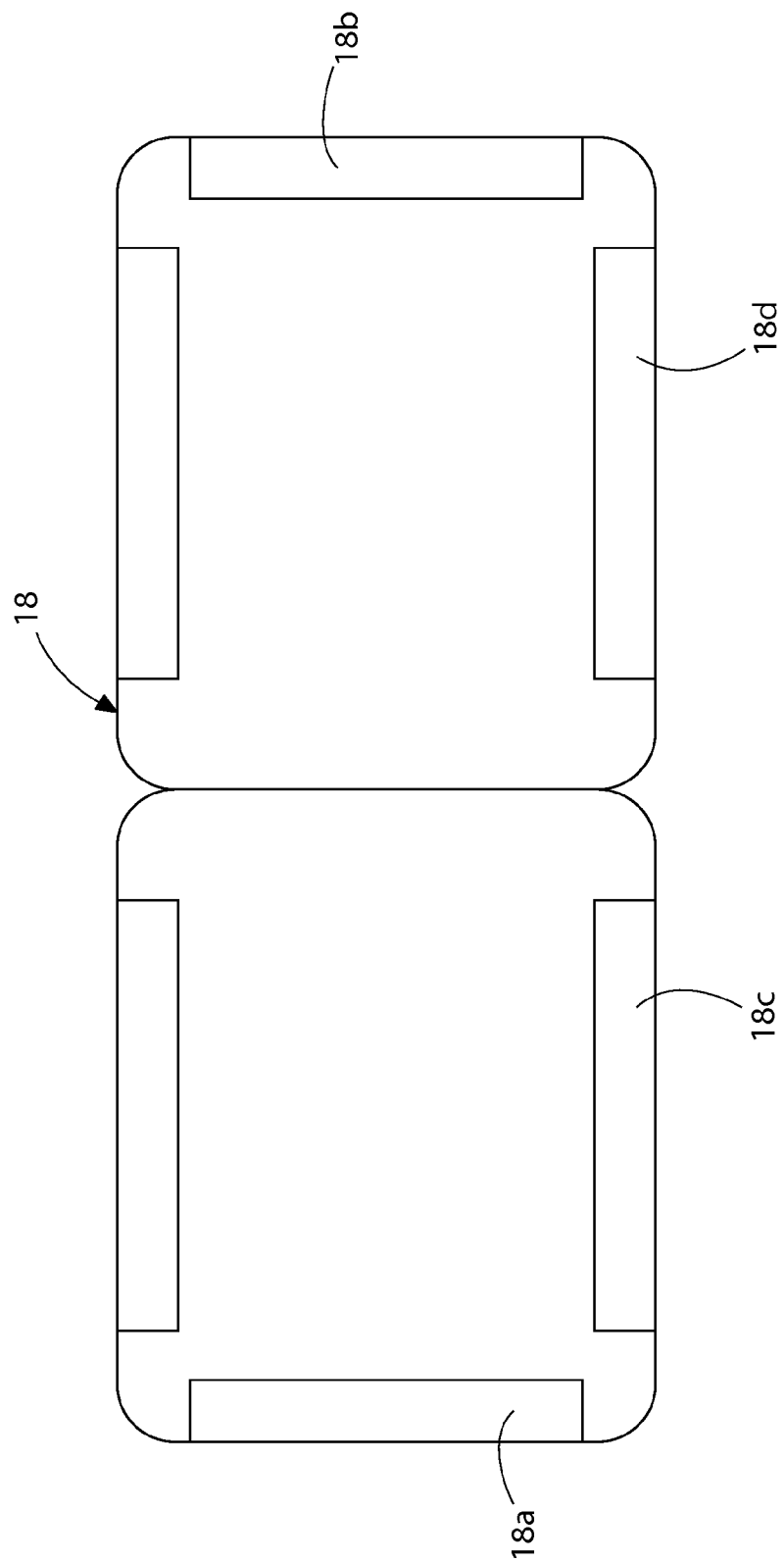
FIG. 6 is a plan view of a fabric envelope that may be used in accordance with one embodiment of the present invention.

Fabric envelope 18 is shown in an open condition in FIG. 6 which is a plan view thereof. From this view, one can appreciate that fabric envelope 18 may be closed over removable secondary dorsal rigid angled support panel 12 once it is placed in the nested position against first rigid angled dorsal support panel 13, such as engagement of hook-and-loop closures 18a with 18b and hook-and-loop closure 18c with 18d.

Figure 7:
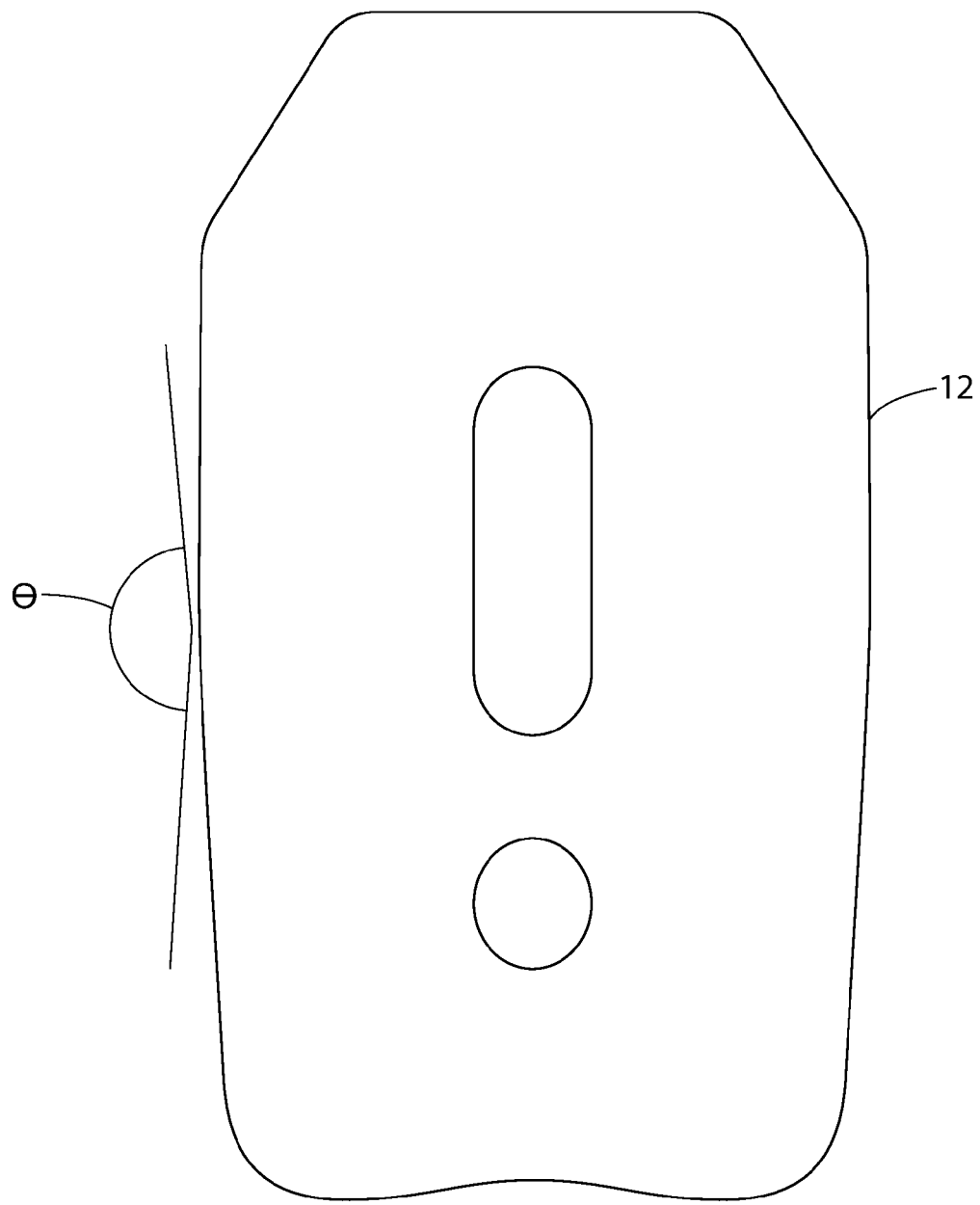
FIG. 7 is an elevation view of a removable secondary dorsal rigid angled support panel that may be used in accordance with one embodiment of the present invention.
Figure 8A:
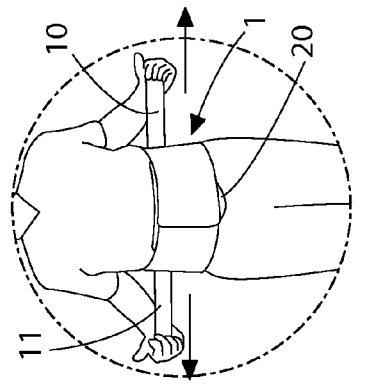
FIG. 8 is a series of perspective views of the stepwise donning and closure of an orthotic brace, in accordance with one embodiment of the present invention.
Figure 8B:
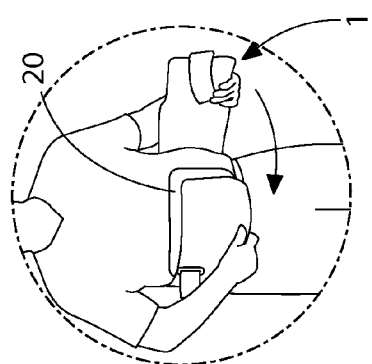
Figure 8C:
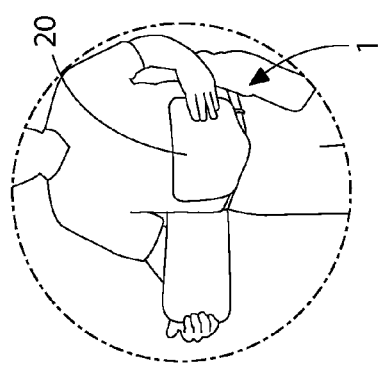
Figure 8D:
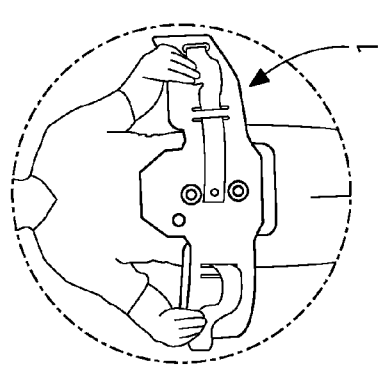
Figure 8E:
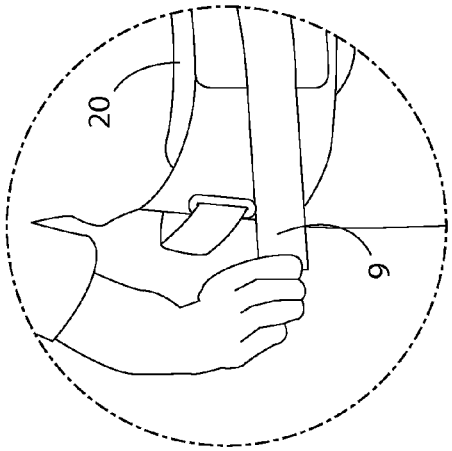
Figure 8F:
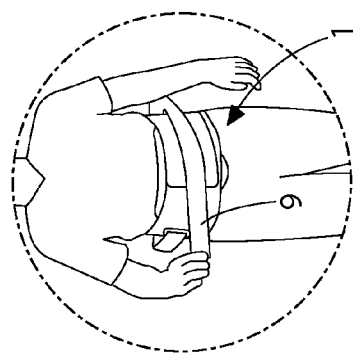
Figure 8G:
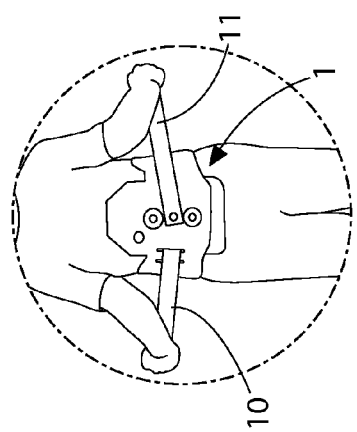

Removable secondary dorsal rigid angled support panel 12 is shown in more detail in FIG. 7. This Figure shows how the support panel 12 is bent at an angle theta (θ), and it is preferred that this angle be in the range of 10-30 degrees preferably 15-25 degrees and most preferably 18 to 23 degrees. This angle will preferably be mirrored in the angling of the first rigid angled dorsal support panel 13 such that the two pieces may be nested most firmly.

The donning of the orthotic brace 1 in accordance with the present invention is shown in stepwise fashion in FIG. 8. To don the device, the wearer will hold the device as shown in step 1 and support it as removable ventral rigid support panel 20 is positioned approximately in front of the wearer's stomach area, as shown in step 2. With panel 20 in position, first and second lateral belt portions are arranged in overlapping relationship such that the hook-and-loop panels 4 and 5 engage one another, as shown in step 3. In step 4, the wearer grasps the D rings of straps 10 and 11 and pulls the straps outwardly and forward such that the first and second lateral belt portions 2 and 3 cinch with respect to one another across the wearer's back. This may also be appreciated from the view in step 5. Once the brace is cinched into a comfortable position, the wearer can close the orthotic brace 1 by closing supplementary strap 9 across the front of the brace as shown in step 6.

Figure 9:
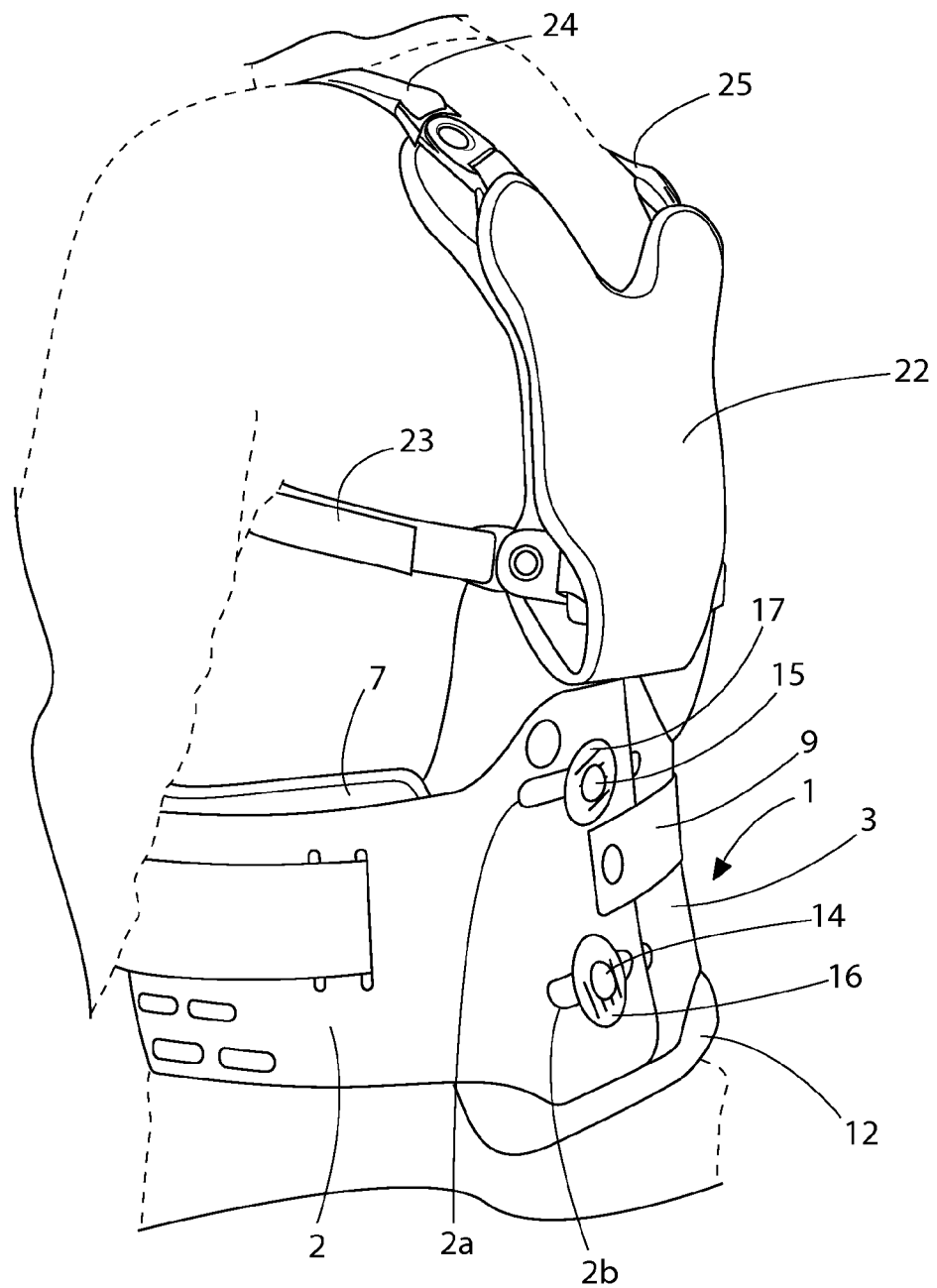
FIG. 9 is a rear quarter perspective view of an orthotic brace in accordance with an optional alternative embodiment of the present invention, as would be seen in a fully closed position on a wearer.

FIG. 9 is a rear quarter perspective view of an orthotic brace 1 in accordance with an optional alternative embodiment of the present invention wherein like reference numerals refer to those portions of the brace described herein. In this optional embodiment, a dorsal thoracic extension portion 22 would be removably attached to the balance of the orthotic brace 1 such as through the use of opposing hook-and-loop panels placed along the top outer surface of moveable secondary dorsal rigid angled support panel 12 (or on the fabric envelope 18 if provided) and on the inner lower surface of the dorsal thoracic extension portion 22. The dorsal thoracic extension portion 22 is provided with straps 23 and 24 that extend the wearer's arms and straps 25 and 26 that extend over the wearer's shoulders (as can be more clearly appreciated in FIG. 10).

Figure 10:
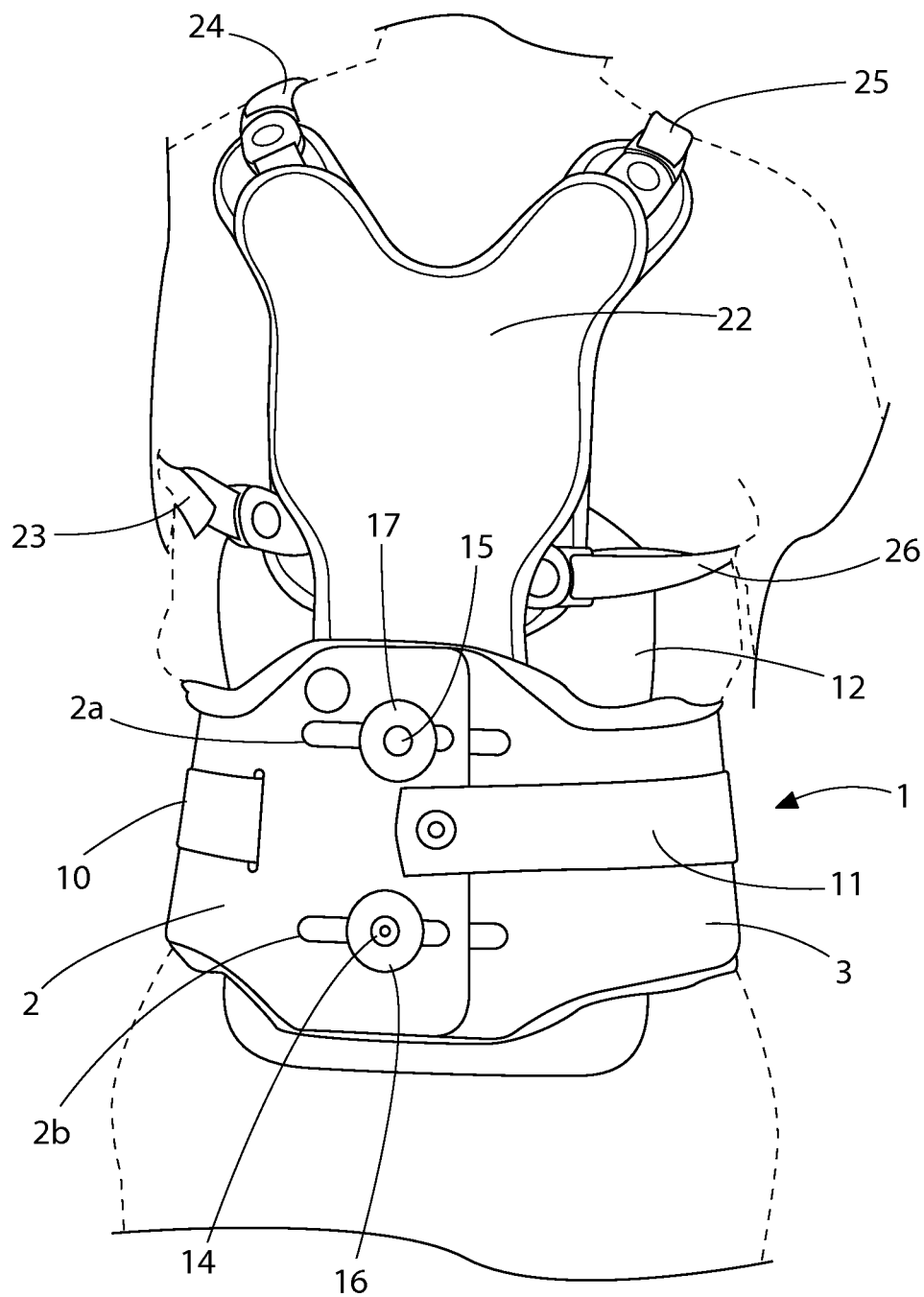
FIG. 10 is a rear perspective view of an orthotic brace in accordance with an optional alternative embodiment of the present invention, as would be seen in a fully closed position on a wearer.

FIG. 10 is a rear perspective view of the orthotic brace 1 in accordance with one embodiment of the present invention, including optional dorsal thoracic extension portion 22, and wherein like reference numerals refer to the portions and features as otherwise described herein.

Figure 11:
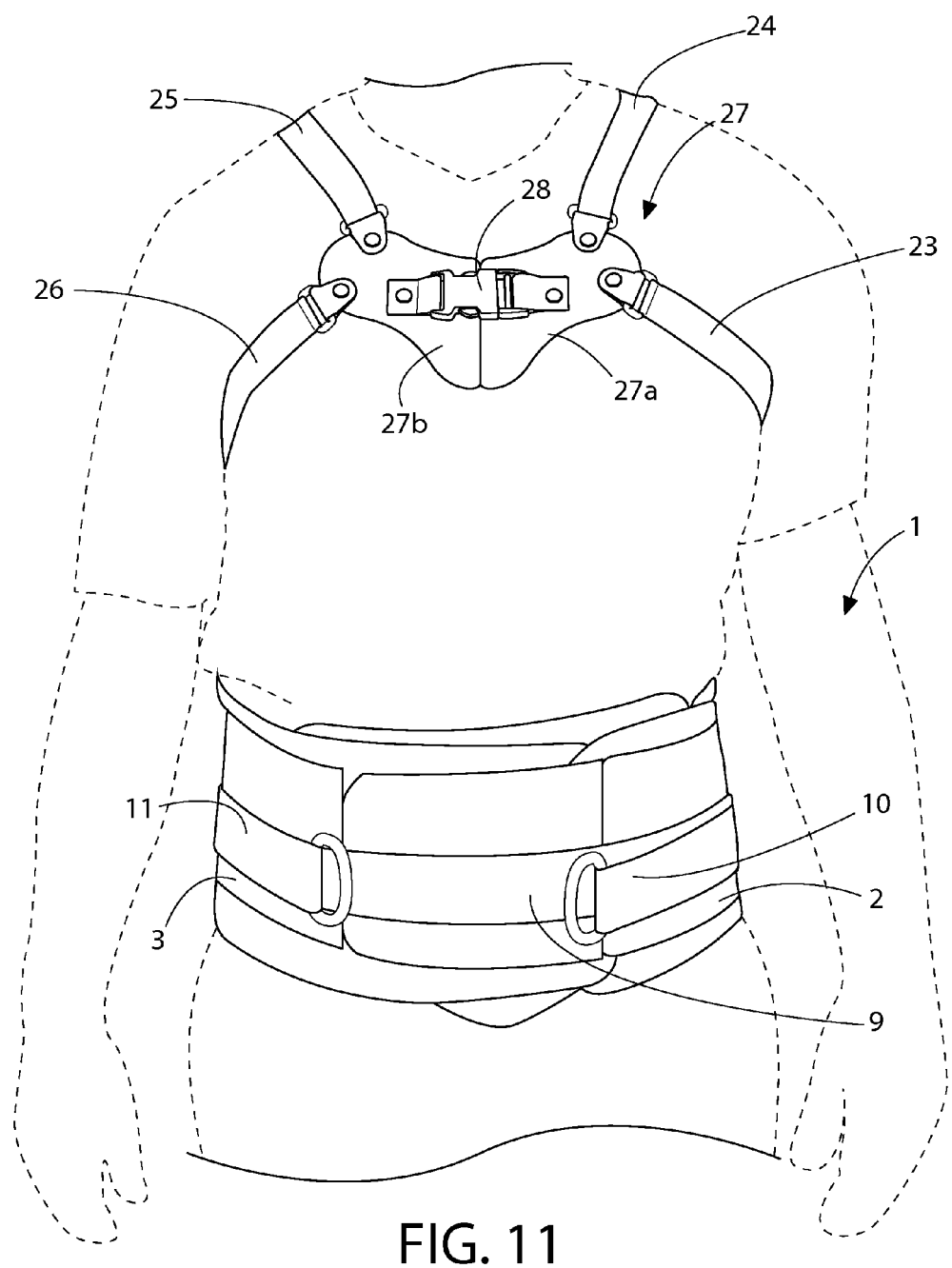
FIG. 11 is a frontal perspective view of an orthotic brace in accordance with an optional alternative embodiment of the present invention, as would be seen in a fully closed position on a wearer.

FIG. 11 is a front perspective view of the orthotic brace in accordance with an optional embodiment of the present invention as shown in FIGS. 9 and 10 and wherein like reference numerals refer to those portions and features already described herein. This figure shows supplemental external support portion 27 comprising a first portion 27a and a second portion 27b. Portion 27a is attached as shown to straps 23 and 24 which are adapted to be adjustable in length. Likewise, portion 27b is attached to straps 25 and 26 that are also adapted to be adjustable in length. Straps 23-26 may be rendered adjustable through any combination or arrangement known in the art. In the displayed embodiment, the straps may be provided with hook-and-loop surfaces so that they may be looped back upon themselves to be of any fixed length to accommodate the thoracic anatomy of the wearer.

Portions 27a and 27b preferably are made to be releasably attached to one another such as by releasable clasp 28. This allows the wearer to adjust and affix the length of straps 23-26 in accordance with the wearer's thoracic anatomy and, once fixed, the upper portion of the orthotic brace may be removed by simply undoing clasp 28 without having to undo any of straps 23-26 so as to maintain their customized fixed length.

Figure 12:
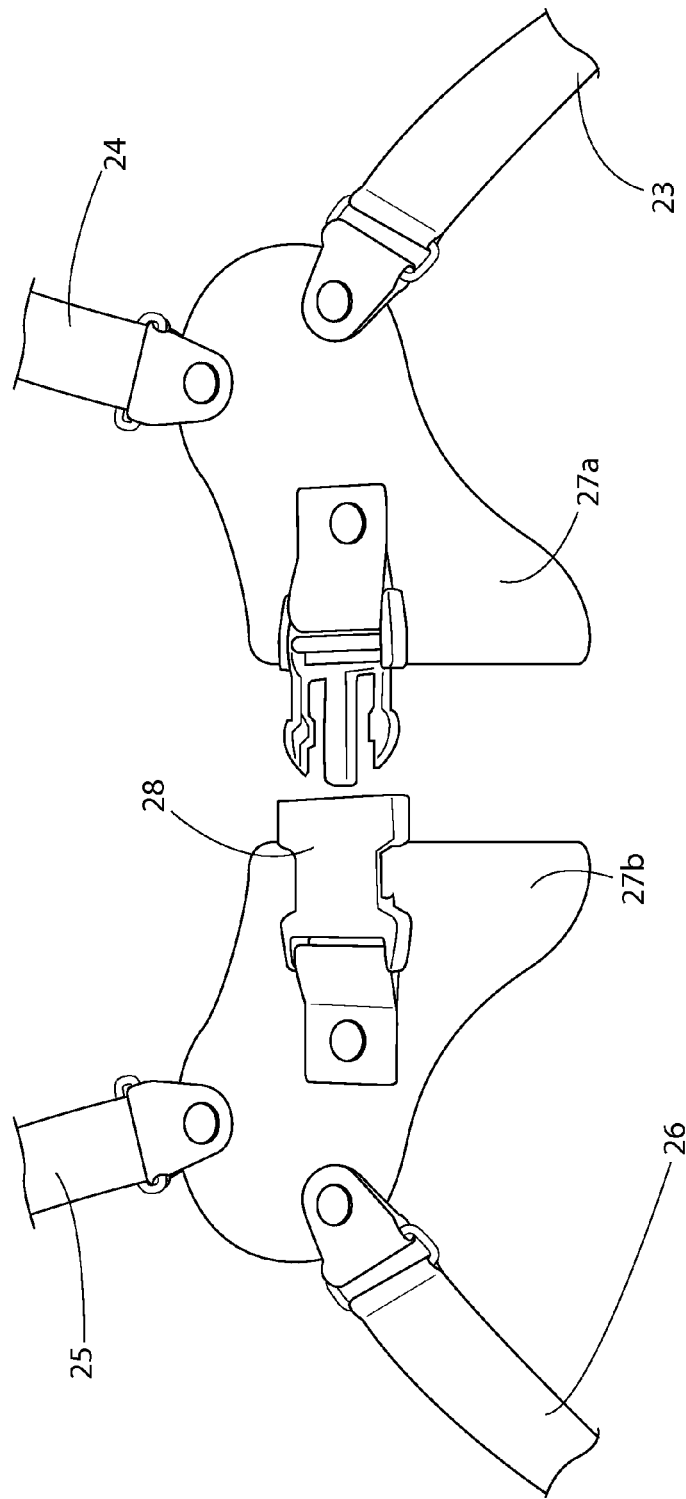
FIG. 12 is a detailed frontal view of a supplemental external support portion of an orthotic brace as shown in FIG. 11 and shown in an open condition.

FIG. 12 is a detailed view of the supplementary external support portion 27 and its associated straps as shown in FIG. 11, and wherein life reference numerals correspond to the portions described herein. From this view, it can be appreciated that the front of the brace can be opened and the top of the orthotic brace removed from the wearer.

Figure 13:
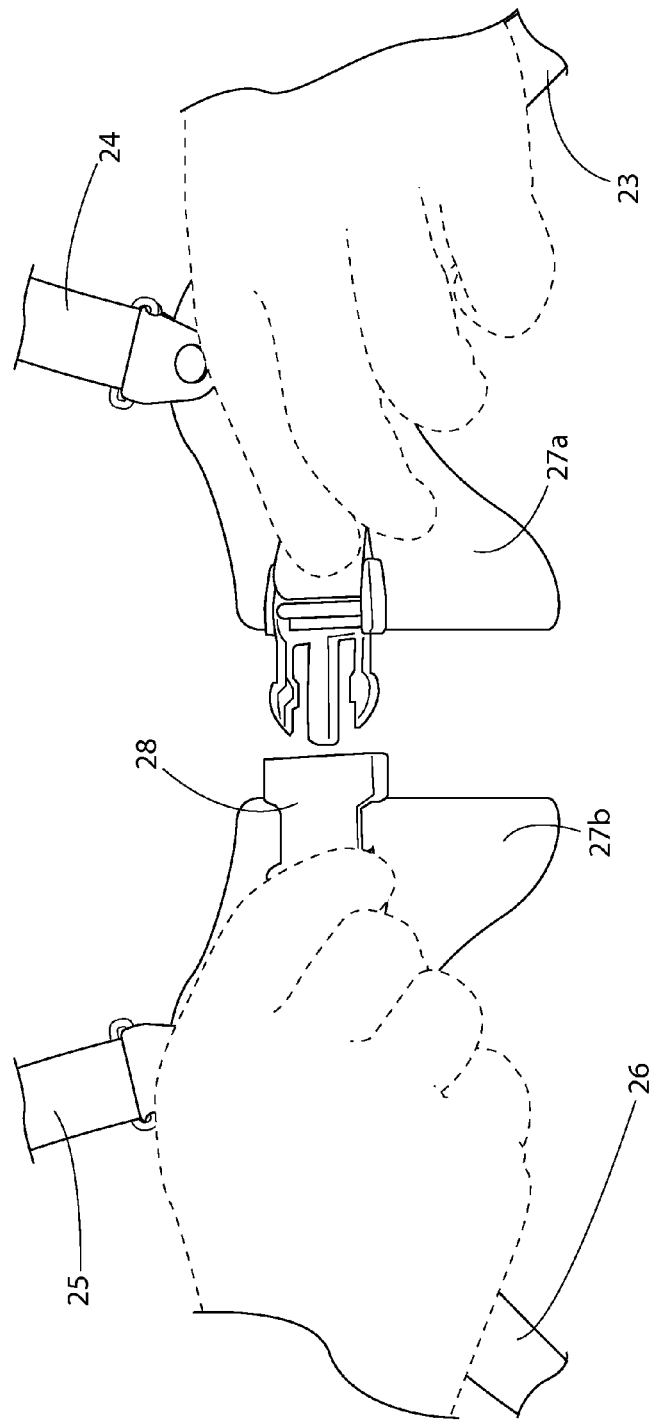
FIG. 13 is a frontal perspective view of a supplementary external support portion of an orthotic brace as shown in FIG. 11, and shown in an open condition being closed by the wearer.

FIG. 13 is a frontal perspective view of the supplementary external support portion of the orthotic brace in accordance with one embodiment of the present invention, and showing the supplementary external portion 27 being closed by the wearer.

Figure 14:
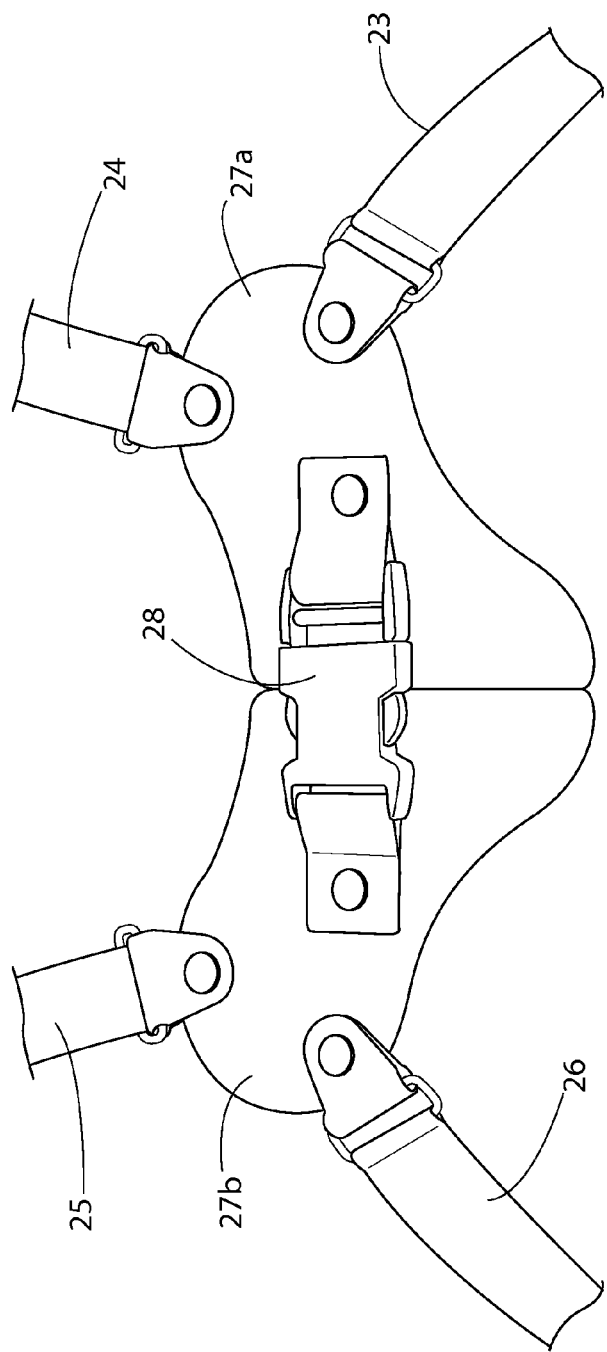
FIG. 14 is a detailed frontal view of a supplemental external support portion of an orthotic brace as shown in FIG. 11 and shown in a closed condition.

FIG. 14 is a frontal perspective view of the supplementary external support portion in a closed condition, wherein like reference numerals identify portions described in FIGS. 12 and 13.

While the invention may be rendered in embodiments in many different forms, there have been shown in the drawings and described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

What is claimed is:

1. A lumbar-sacral orthosis comprising in combination,
   a. a first lateral belt portion having a dorsal end having two substantially parallel horizontally extending upper and lower slots, and an inner surface bearing a pad;
   b. a second lateral belt portion having a dorsal end having two substantially parallel horizontally extending upper and lower slots, and an inner surface bearing a pad;
      said first and second lateral belt portions adapted to overlap across the wearer's ventral area when said orthotic brace is donned, and to be releasably attached to one another,
   c. a central dorsal portion, said central dorsal portion attached to said first and second lateral belt portions by an upper pin extending from said central dorsal portion through said upper slots, and a lower pin extending from said central dorsal portion through said lower slots, such that said first and second lateral belt portions may be moved with respect to one another; said central dorsal portion comprising, along its inner-facing surface, a first rigid angled dorsal support panel, said first rigid angled support panel incorporated into said central dorsal portion such that it opens away from the wearer, when said orthosis is donned;
   d. a removable secondary dorsal rigid angled support panel, larger than said first rigid angled dorsal support panel, and adapted to be nested against said first rigid angled dorsal support panel and along its inner-facing surface;
   e. a removable ventral rigid support panel and adapted to be removably attached to the inside of said overlapping first and second lateral belt portions when said orthosis is donned;
   f. a first strap attached to said second belt portion and extending over said first lateral belt portion, and adapted to be releasably attached to said ventral portion of said orthosis when donned; and
   g. a second strap attached to said first belt portion and extending over said second lateral belt portion, and adapted to be releasably attached to said ventral portion of said orthosis when donned.

2. A lumbar-sacral orthosis according to claim 1 wherein said removable secondary dorsal rigid angled support panel is contained in a fabric envelope and is removably nested against said first rigid angled dorsal support panel and along its inner-facing surface by hook and loop closures.

3. A lumbar-sacral orthosis according to claim 1 wherein said first rigid angled dorsal support panel comprises a material covering its inner surface and wherein said removable secondary dorsal rigid angled support panel is removably nested against said first rigid angled dorsal support panel and along its material-covered inner-facing surface by hook and loop closures.

4. A lumbar-sacral orthosis according to claim 1 wherein said removable ventral rigid support panel is contained in a fabric envelope and is removably nested against said first rigid angled dorsal support panel and along its inner-facing surface by hook and loop closures.

5. A lumbar-sacral orthosis according to claim 1 wherein said orthosis additionally comprises a removable supplementary ventral support portion comprising (a) an extension portion extending anteriorly from said ventral region of said orthosis, and (b) a supplementary ventral support panel adapted to be affixed along said extension portion and to engage the wearer when said orthosis is donned.

6. A lumbar-sacral orthosis according to claim 5 wherein said supplementary ventral support panel is adapted to be fixed at two or more points along the length of said extension portion.

7. A lumbar-sacral orthosis according to claim 1 wherein said removable ventral rigid support panel additionally comprises a removable supplementary ventral support portion comprising (a) an extension portion extending anteriorly from said ventral region of said orthosis, and (b) a supplementary ventral support panel adapted to be affixed to said extension portion and to engage the wearer when said orthosis is donned.

8. A lumbar-sacral orthosis according to claim 7 wherein said supplementary ventral support panel is adapted to be fixed at two or more points along the length of said extension portion.

9. A lumbar-sacral orthosis according to claim 1 wherein said removable ventral rigid support panel additionally comprises a removable supplementary ventral support portion contained in a fabric envelope.

10. A lumbar-sacral orthosis according to claim 1 wherein said first and second straps are adapted to be releasably attached to said ventral portion of said orthosis by hook and loop closures.

11. A lumbar-sacral orthosis according to claim 1 wherein said dorsal ends of said first and second lateral belt portions, and said central dorsal portion are wrapped in a removable material envelope adapted to function as a component of a hook and loop closure.

12. A lumbar-sacral orthosis according to claim 1 wherein said dorsal ends of said first and second lateral belt portions, said central dorsal portion and said removable secondary dorsal rigid angled support panel are wrapped in a removable material envelope adapted to function as a component of a hook and loop closure.

13. A lumbo-sacral orthopedic brace in accordance with claim 1 wherein said removable secondary dorsal rigid angled support panel comprises a polymer material.

14. A lumbo-sacral orthopedic brace in accordance with claim 1 wherein said first rigid angled dorsal support panel comprises a polymer material.

15. A lumbo-sacral orthopedic brace in accordance with claim 1 wherein said removable ventral rigid support panel comprises a polymer material.

16. A lumbar-sacral orthosis comprising in combination,
    a. a first lateral belt portion having a dorsal end having two substantially parallel horizontally extending upper and lower slots, and an inner surface bearing a pad;
    b. a second lateral belt portion having a dorsal end having two substantially parallel horizontally extending upper and lower slots, and an inner surface bearing a pad;
       said first and second lateral belt portions adapted to overlap across the wearer's ventral area when said orthosis is donned, and to be releasably attached to one another,
    c. a central dorsal portion, said central dorsal portion attached to said first and second lateral belt portions by an upper pin extending from said central dorsal portion through said upper slots, and a lower pin extending from said central dorsal portion through said lower slots, such that said first and second lateral belt portions may be moved with respect to one another; said central dorsal portion comprising, along its inner-facing surface, a first rigid angled dorsal support panel, said first rigid angled support panel incorporated into said central dorsal portion such that it opens away from the wearer, when said orthosis is donned;

d. a removable secondary dorsal rigid angled support panel, larger than said first rigid angled dorsal support panel, and adapted to be nested against said first rigid angled dorsal support panel and along its inner-facing surface;
e. a removable ventral rigid support panel and adapted to be removably attached to the inside of said overlapping first and second lateral belt portions when said orthosis is donned;
f. a first strap attached to said second belt portion and extending over said first lateral belt portion, and adapted to be releasably attached to said ventral portion of said orthosis when donned;
g. a second strap attached to said first belt portion and extending over said second lateral belt portion, and adapted to be releasably attached to said ventral portion of said orthosis when donned;
    said first and second straps attached so as to permit the wearer to tighten said belt portions;
h. a dorsal thoracic extension portion removably attached to said removable secondary dorsal rigid angled support panel;
i. a supplementary sternal support portion connected to said dorsal thoracic extension portion by four arm straps, two of which are adapted to extend under the wearer's arms and two of which are adapted to extend over the wearer's shoulder.

17. A lumbar-sacral orthosis according to claim 16 wherein said supplementary sternal support portion is in the form of two portions releasably connected to one another so as to allow the wearer to remove said lumbar-sacral orthosis without disconnecting said arm straps.

* * * * *